United States Patent
Li

(10) Patent No.: US 11,717,270 B2
(45) Date of Patent: Aug. 8, 2023

(54) METHOD, APPARATUS AND SYSTEM FOR IMAGING IN ULTRASONIC SCANNING

(71) Applicant: SHENZHEN MINDRAY BIO-MEDICAL ELECTRONICS CO., LTD., Guangdong (CN)

(72) Inventor: Shuangshuang Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 183 days.

(21) Appl. No.: 16/619,644

(22) PCT Filed: Jun. 6, 2017

(86) PCT No.: PCT/CN2017/087345
§ 371 (c)(1),
(2) Date: May 4, 2020

(87) PCT Pub. No.: WO2018/223294
PCT Pub. Date: Dec. 13, 2018

(65) Prior Publication Data
US 2020/0268356 A1 Aug. 27, 2020

(51) Int. Cl.
*A61B 8/00* (2006.01)
*A61B 8/14* (2006.01)
(Continued)

(52) U.S. Cl.
CPC ............... *A61B 8/54* (2013.01); *A61B 8/14* (2013.01); *A61B 8/4483* (2013.01); *A61B 8/461* (2013.01); *A61B 8/485* (2013.01); *G01S 15/8934* (2013.01)

(58) Field of Classification Search
CPC .......... A61B 8/54; A61B 8/14; A61B 8/4483; A61B 8/461; A61B 8/485; A61B 8/5207;
(Continued)

(56) References Cited

U.S. PATENT DOCUMENTS 4,442,713 A * 4/1984 Wilson ................ G01S 15/8954
73/626
5,421,333 A 6/1995 Takamizawa et al.
(Continued)

FOREIGN PATENT DOCUMENTS

CN 1809399 A 7/2006
CN 101190133 A 6/2008
(Continued)

OTHER PUBLICATIONS

PCT International Preliminary Report on Patentability dated Dec. 19, 2019, issued in related International Application No. PCT/CN2017/087345, with partial English translation (10 pages).
(Continued)

*Primary Examiner* — Christopher Koharski
*Assistant Examiner* — Taylor Deutsch
(74) *Attorney, Agent, or Firm* — Sheppard Mullin Richter & Hampton LLP

(57) ABSTRACT

A method comprises: generating a shear wave in a target tissue; selecting an ultrasound transducer group in an ultrasound probe, and determining a focus position and a transmitting aperture corresponding to the ultrasound transducer group, such that a sound field boundary range formed by the ultrasound transducer group completely covers a region of interest in the target tissue; controlling the array elements to transmit ultrasound waves according to the corresponding relative time delays, so as to cause a transmitting focusing effect; receiving ultrasound echoes returned from the region of interest, obtaining echo information of different positions in the region of interest, and obtaining, according to the echo information, shear wave information corresponding to the region of interest.

16 Claims, 8 Drawing Sheets

(51) Int. Cl.
*A61B 8/08* (2006.01)
*G01S 15/89* (2006.01)

(58) Field of Classification Search
CPC ..... A61B 8/4488; A61B 8/085; A61B 8/4411; A61B 8/469; A61B 8/4494; G01S 15/8934; G01S 7/5206; G01S 15/8927; G01S 7/52042

See application file for complete search history.

(56) References Cited

U.S. PATENT DOCUMENTS

| | | | |
|---|---|---|---|
| 5,827,188 | A | 10/1998 | Wright et al. |
| 8,001,843 | B2 | 8/2011 | Yao et al. |
| 8,057,393 | B2 | 11/2011 | Yao et al. |
| 8,088,068 | B2 | 1/2012 | Yao et al. |
| 8,317,704 | B2 | 11/2012 | Robert et al. |
| 10,390,797 | B2 | 8/2019 | Shi et al. |
| 10,695,030 | B2 | 6/2020 | Clark et al. |
| 2002/0143253 | A1* | 10/2002 | Robinson ............ G01S 7/52077 600/437 |
| 2007/0038091 | A1 | 2/2007 | Shiki |
| 2007/0088213 | A1* | 4/2007 | Poland ................... G10K 11/34 600/437 |
| 2008/0125660 | A1* | 5/2008 | Yao ....................... G01S 7/5202 600/459 |
| 2010/0256488 | A1* | 10/2010 | Kim ........................ A61B 8/488 600/439 |
| 2010/0331690 | A1 | 12/2010 | Li et al. |
| 2012/0108968 | A1 | 5/2012 | Freiburger et al. |
| 2015/0192547 | A1* | 7/2015 | Lee .......................... A61B 8/485 73/641 |
| 2017/0296140 | A1 | 10/2017 | Ebbini et al. |
| 2017/0311929 | A1 | 11/2017 | Shao et al. |
| 2018/0296190 | A1* | 10/2018 | Susumu ................ A61B 8/5269 |

FOREIGN PATENT DOCUMENTS

| | | |
|---|---|---|
| CN | 101190134 A | 6/2008 |
| CN | 101396282 A | 4/2009 |
| CN | 101442938 A | 5/2009 |
| CN | 101474079 A | 7/2009 |
| CN | 101632583 A | 1/2010 |
| CN | 101690677 A | 4/2010 |
| CN | 101756713 A | 6/2010 |
| CN | 103156636 A | 6/2013 |
| CN | 103269639 A | 8/2013 |
| CN | 103462643 A | 12/2013 |
| CN | 103747742 A | 4/2014 |
| CN | 103857342 A | 6/2014 |
| CN | 103969651 A | 8/2014 |
| CN | 104825195 A | 8/2015 |
| CN | 105212968 A | 1/2016 |
| CN | 105433945 A | 3/2016 |
| CN | 105796126 A | 7/2016 |
| JP | 2009-297399 A | 12/2009 |
| WO | 2013/088326 A1 | 6/2013 |
| WO | 2016160981 A1 | 10/2016 |

OTHER PUBLICATIONS

First Search dated Feb. 14, 2020, issued in related Chinese Application No. 201780018490.X (1 page).

First Office Action dated Feb. 19, 2020, issued in related Chinese Application No. 201780018490.X, with English machine translation (24 pages).

PCT International Search Report and the Written Opinion dated Feb. 27, 2018, issued in related International Application No. PCT/CN2017/087345, with partial English translation (9 pages).

First Search dated Nov. 2, 2020, issued in related Chinese Application No. 202010769292.0 (2 pages).

First Office Action dated Nov. 9, 2020, issued in related Chinese Application No. 202010769292.0, with English machine translation (20 pages).

Jin Ho Chang et al, "A New Synthetic Aperture Focusing Method to Suppress the Diffraction of Ultrasound", IEEE Transactions on Ultrasonics, Ferroelectrics, and Frequency Control, vol. 58, No. 2, Feb. 28, 2011, pp. 327-337.

Wang Ping et al., "The method of dual focusing beamforming based on virtual element in ultrasound imaging", Journal of Chongqing University, vol. 36, No. 5, May 31, 2013, pp. 75-79.

Second Office Action dated May 25, 2020, issued in related Chinese Application No. 201780018490 X, with English machine translation (8 pages).

Supplementary Search dated Jan. 15, 2021, issued in related Chinese Application No. 202010769292.0 (2 pages).

* cited by examiner

METHOD, APPARATUS AND SYSTEM FOR IMAGING IN ULTRASONIC SCANNING

CROSS REFERENCE TO RELATED APPLICATION

The present application is a U.S. national phase application of International Application No. PCT/CN2017/087345, filed with the China National Intellectual Property Administration on Jun. 6, 2017 and entitled "Method, Apparatus and System for Imaging in Ultrasonic Scanning", which is incorporated herein by reference in its entirety.

TECHNICAL FIELD

The present disclosure relates to medical technology, particularly to imaging methods, apparatuses and systems in ultrasound scanning.

BACKGROUND

Ultrasound elastography is one of the hotspots in clinical research in recent years. It can present the elasticity or hardness of tissues, and has been used more and more in the auxiliary detection, benign and malignant discrimination and prognosis evaluation, etc. of tissue cancer.

The existing ultrasound shear wave elastography technology mainly presents the difference in hardness between tissues by generating shear wave propagation in the tissue and detecting the propagation parameters (such as propagation velocity). For an isotropic elastic tissue, there is the following relationship between the propagation velocity of the shear wave and the elastic modulus of the tissue: Young's modulus $E=3\rho C_s^2$, where, Cs represents the propagation velocity of the shear wave in the tissue, and $\rho$ is the tissue density. It can be seen that there is a one-to-one correspondence between shear wave velocity and elastic modulus. Because this method can obtain quantitative hardness measurement results, which can make the doctor's diagnosis more convenient and objective, it has been widely concerned and welcomed by doctors.

However, in order to accurately calculate the shear wave propagation velocity in the region of interest, the ultrasound system usually needs to quickly and continuously obtain the ultrasound echo information at the times within a period of time so as to accurately detect the arrival position of the shear wave at the times, which requires that the system can obtain all the information in the region of interest in a very short time. In the conventional ultrasound imaging method, the detection range of the ultrasound echoes received by a single transmitting and receiving is very narrow, and it is difficult to meet the requirement.

SUMMARY

The present disclosure provides methods, apparatuses and systems for imaging in ultrasound scanning, which can obtain accurate echo information and effectively improve the imaging frame rate and signal quality, and can be widely used.

In one embodiment, a method for imaging in ultrasound scanning is provided, which may include:

generating a shear wave in a target tissue which propagates in a region of interest;

selecting at least one ultrasound transducer group in an ultrasound probe and determining a focus position and a transmitting aperture of the ultrasound transducer group according to a depth and width of the region of interest in the target tissue, such that a sound field generated by the at least one ultrasound transducer group completely covers the region of interest in the target tissue;

determining a relative time delay between transmitting of transducers in the ultrasound transducer group and controlling the transducers in the ultrasound transducer group to transmit ultrasound waves according to the relative time delay, such that the ultrasound waves transmitted by the transducers in the ultrasound transducer group arrive the focus position at the same time, thereby achieving an transmitting focusing;

receiving ultrasound echoes from the region of interest to obtain echo information at different positions in the region of interest at different times during a duration; and obtaining a shear wave information corresponding to the region of interest according to the echo information.

In one embodiment, an apparatus for imaging in ultrasound scanning is provided, which may include:

a shear wave control unit configured to generate a shear wave in a target tissue which propagates in a region of interest;

a transmitting focusing control unit configured to select at least one ultrasound transducer group in the ultrasound probe and determine a focus point and a transmitting aperture of the ultrasound transducer group according to a depth and a width of the region of interest in the target tissue, such that a sound field generated by the at least one ultrasound transducer group completely covers the region of interest in the target tissue;

a transmitting control unit configured to determine a relative time delay between transmitting of transducers in the ultrasound transducer group and control the transducers in the ultrasound transducer group to transmit ultrasound waves according to the relative time delay, such that the ultrasound waves transmitted by the transducers in the ultrasound transducer group arrive the focus position at the same time, thereby achieving a transmitting focusing;

a receiving control unit configured to receive ultrasound echoes from the region of interest during a duration to obtain echo information at different positions in the region of interest at different times; and an imaging processing unit configured to obtain a shear wave information corresponding to the region of interest according to the echo information obtained by the receiving control unit.

In one embodiment, an ultrasound imaging system is provided, which may include:

an ultrasound probe which comprises at least one ultrasound transducer group;

a transmitting and receiving circuit which excites the ultrasound probe to transmit an ultrasound beam to a target tissue and receive echoes of the ultrasound beam to obtain echo signals;

a memory which stores a computer program;

a processor which executes the computer program in the memory to:

control the ultrasound probe through the transmitting and receiving circuit to generate a shear wave in a target tissue which propagates in a region of interest;

select at least one ultrasound transducer group in the ultrasound probe and determine a focus point and a transmitting aperture of the ultrasound transducer group according to a depth and a width of the region of interest in the target tissue, such that a sound field generated by the at least one ultrasound transducer group completely covers the region of interest in the target tissue;

determine a relative time delay between transmitting of transducers in the ultrasound transducer group and control the transducers in the ultrasound transducer group through the transmitting and receiving circuit to transmit ultrasound waves according to the relative time delay, such that the ultrasound waves transmitted by the transducers in the ultrasound transducer group arrive the focus position at the same time, thereby achieving a transmitting focusing;

receive ultrasound echoes from the region of interest during a duration to obtain echo information at different positions in the region of interest at different times; and obtain a shear wave information corresponding to the region of interest according to the echo information obtained by the receiving control unit; and a display which displays an image generated by the imaging processing unit.

In the methods, apparatuses and systems for imaging in ultrasound scanning in the embodiments of the present disclosure, at least one ultrasound transducer group may be selected in the ultrasound probe and the focus positions and transmitting apertures of the ultrasound transducer groups may be determined according to the depth and width of the region of interest, such that the sound field generated by the at least one ultrasound transducer group completely covers the region of interest in the target tissue. The transducers in the ultrasound transducer group may be controlled to transmit the ultrasound waves according to the corresponding relative time delay, such that the ultrasound waves transmitted by the transducers in the ultrasound transducer group arrive the corresponding focus position at the same time, thereby achieving the transmitting focusing. Therefore, the ultrasound energy in the region of interest is uniform, and accurate echo information can be obtained.

Furthermore, by adjusting the parameters of the ultrasound scanning and weighting the echo signals obtained under different parameters, the signal-to-noise ratio of the echo signals can be improved, thereby improving the signal quality.

BRIEF DESCRIPTION OF THE DRAWINGS

In order to more clearly describe the embodiments of the present disclosure or the technical solutions in the prior art, the drawings to be used in the description of the embodiments of the present disclosure or the prior arts will be briefly described below. Obviously, the drawings in the following description are only some embodiments of the present disclosure. For those ordinarily skilled in the art, other drawings may be obtained based on these drawings without any creative labor.

DETAILED DESCRIPTION

The technical solutions in the embodiments of the present disclosure will be described clearly and completely in conjunction with the drawings. However, the described embodiments are only a part, but not all, of the embodiments of the present disclosure. All other embodiments obtained by those ordinarily skilled in the art based on the embodiments of the present disclosure without creative work will fall within the protection scope of the present disclosure.

The embodiments of the present disclosure will be described below with reference to the drawings, and the system block diagram shown in FIG. 12 or FIG. 14.

Figure 1:
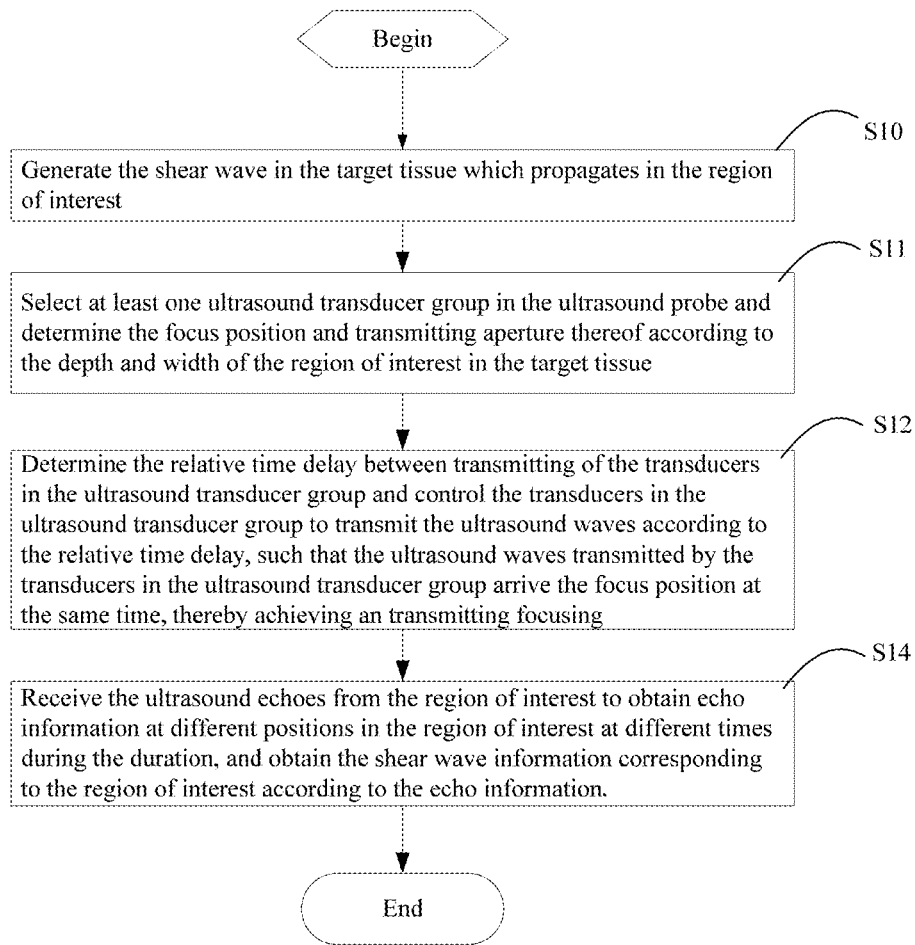
FIG. 1 is a schematic flowchart of one embodiment of a method for imaging in ultrasound scanning provided by the present disclosure.

FIG. 1 is a schematic flowchart of one embodiment of the method for imaging in ultrasound scanning provided by the present disclosure. In this embodiment, the method for imaging in ultrasound scanning may include the following steps.

In step S10, the ultrasound probe may be controlled by the transmitting circuit and the receiving circuit to generate a shear wave in the target tissue which propagates in the region of interest in the target tissue. For example, the shear wave may be generated by transmitting ultrasound beams into the target tissue and propagate in the region of interest in the target tissue.

In step S11, according to the depth and width of the region of interest in the target tissue, at least one ultrasound transducer group in the ultrasound probe may be selected, and the focus positions and the transmitting apertures (the width of the transmitting transducers in the ultrasound transducer groups) corresponding to the ultrasound transducer groups may be determined, such that the sound field generated by the at least one ultrasound transducer group completely covers the region of interest in the target tissue. The at least one sound field corresponding to the at least one ultrasound transducer group may be respectively focused at the corresponding focus position, and such at least one sound field may be superimposed to form the sound field that completely covers the region of interest. The ultrasound probe may be a linear probe or an matrix probe.

It can be understood that, in different embodiments, the number of the ultrasound transducer group, the transmitting aperture and the number and position of the focus point may be determined according to the depth and width of the region of interest.

Figure 2:
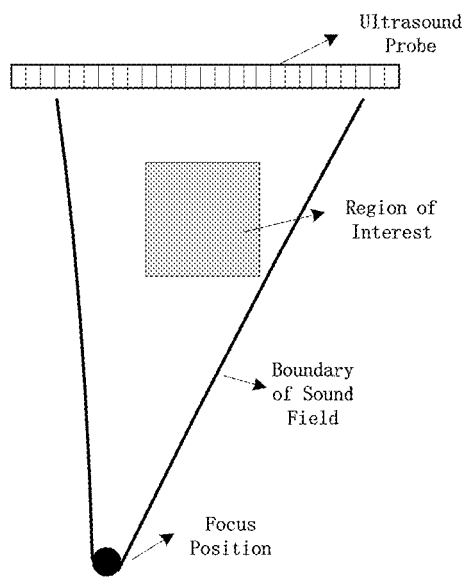
FIG. 2 is a schematic diagram of one embodiment of selecting an ultrasound transducer group and a focus position in FIG. 1.

For example, in the embodiment of FIG. 2, one ultrasound transducer group and one focus position are selected, where the depth of the focus position corresponding to the ultrasound transducer group is greater than the depth of the region of interest. Therefore, the sound field generated by such ultrasound transducer group completely covers the region of interest in the target tissue.

Figure 3:
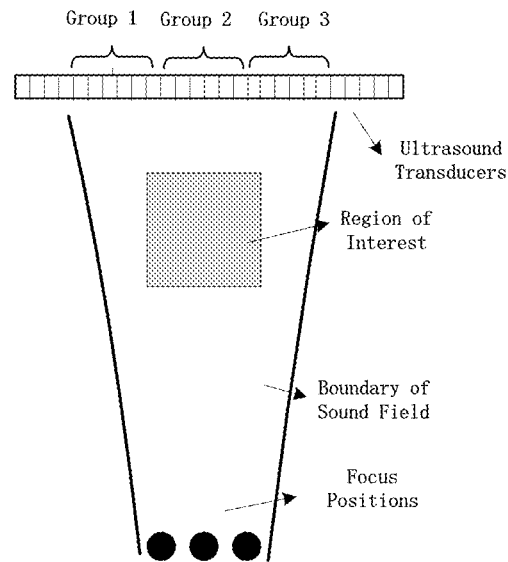
FIG. 3 is a schematic diagram of another embodiment of selecting an ultrasound transducer group and a focus position in FIG. 1.

In the embodiment of FIG. 3, three ultrasound transducer groups are selected, and each ultrasound transducer group corresponds to one focus position. In the figure, the selected focus points are on one straight line. The selected focus points are symmetrically with respect to the region of interest, and the depths of the focus positions corresponding to the ultrasound transducer groups are greater than the depth of the region of interest. The sound field generated by these ultrasound transducer groups completely covers the region of interest in the target tissue. Since the ultrasound waves transmitted by these ultrasound transducer groups are respectively focused at different focus points and these focus points are on a straight line, the energy distribution of the sound field is more uniform. Therefore, the energy distribution of the sound field in the region of interest is also uniform. In addition, since the transmitting transducer group on the side is relatively far from the focus point, the number of transducers in such transmitting transducer group can be increased. It can be understood that the number of the transducers in the ultrasound transducer groups may not necessarily be the same, but can be adjusted appropriately according to the strength of the focusing.

Figure 4:
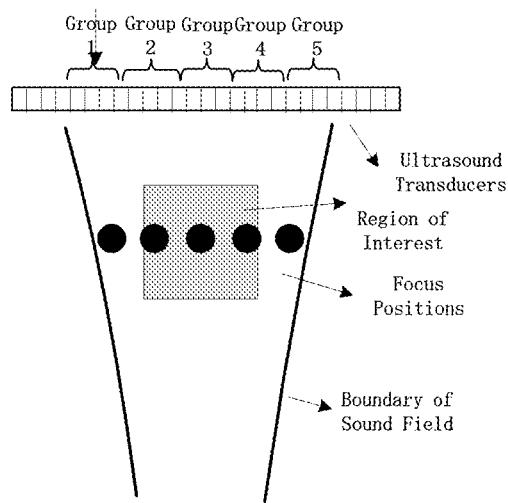
FIG. 4 is a schematic diagram of another embodiment of selecting an ultrasound transducer group and a focus position in FIG. 1.

In the embodiment of FIG. 4, five ultrasound transducer groups are selected, and each ultrasound transducer group corresponds to a focus position. The depths of the focus positions corresponding to the ultrasound transducer groups are within the depth range of the region of interest, and the width formed by all focus points is greater than the width of the region of interest. Therefore, the sound field generated by these ultrasound transducer groups completely covers the region of interest in the target tissue, and the energy distribution is uniform.

It can be understood that, as long as the appropriate focus width, focus depth and transmitting aperture are determined, whether the focus depth is within or outside the depth range of the region of interest, or less or greater than the depth of the region of interest, and whether the focus points are in a straight line or a specific curve, an desired sound field coverage effect may be achieved. The methods of the present disclosure may also be applicable to ultrasound transducer groups arranged in different shapes, such as linear arrangement, convex arrangement and circular arrangement, etc.

In some embodiments, it is not necessary that the focus positions are symmetrical with respect to the region of interest. For example, FIG. 2 shows asymmetrically focus positions, which results in an effect similar to the effect of transmitting with the symmetrical focus positions steered by a certain angle. Therefore, it may also be possible to calculate a new focus position by steering a certain angle based on the symmetrical focus positions above.

After the focus position is determined, appropriate transducers in the probe may be determined to perform the transmitting to achieve the suitable focusing strength. The focusing strength may be determined according to the F-number index. The width of the transmitting transducers may also be referred to as the transmitting aperture.

$F\text{-number} = \text{depth of focus} / \text{transmitting aperture}$

The larger the F-number, the weaker the focusing, and the wider and more dispersed the sound field at the focal zone;

The smaller the F-number, the stronger the focusing, and the narrower and more concentrated the sound field at the focal zone;

The number of transducers in the ultrasound transducer group may be the same.

Figure 5:
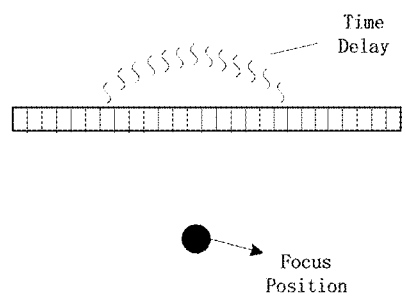
FIG. 5 is a schematic diagram of determining the relative time delay of transmitting ultrasound waves between the transducers in the ultrasound transducer group in FIG. 1.

In step S12, the relative time delay between the ultrasound transmitting of the transducers in the ultrasound transducer group may be determined, and the transmitting circuit may control the transducers in the ultrasound transducer group to transmit the ultrasound waves according to the corresponding time delay (i.e., the transmitting sequence, relative time interval, etc.), such that the ultrasound waves transmitted by the transducers in each ultrasound transducer group arrive the corresponding focus points at the same time, thereby achieving the transmitting focusing. Specifically, according to the geometric relationship between each focus point and the transducers of the ultrasound probe, the differences between the times when the ultrasound waves transmitted by the transducers arrive their focus points may be calculated. Such time differences may be compensated in the transmitting start time, thereby determining the relative time delay between the ultrasound wave transmitting of the transducers in the ultrasound transducer group. For example, FIG. 5 shows a schematic diagram for determining the relative time delay between the ultrasound wave transmitting of the transducers in the ultrasound transducer group. It can be seen that the transducer far away from the focus point need to transmit first and the transducer close to the focus point need to transmit later. Finally, the ultrasound waves transmitted by all transducers may arrive the focus point at the same time.

In one embodiment, in order to achieve a better ultra-wide coverage, multiple ultrasound transducer groups may respectively correspond to multiple focus positions and the multiple focus positions may be arranged laterally along the shear wave propagation direction.

In order to enable the sound field generated by the focused transmitting to completely cover the region of interest, in one embodiment, the depths of the focus positions corresponding to the ultrasound transducer groups may be greater than the depth of the region of interest. Alternatively, the depths of the focus positions corresponding to the ultrasound transducer groups may be within the depth range of the region of interest and the width formed by all focus positions arranged along the shear wave propagation direction may be greater than the width of the region of interest.

In addition, during the transmitting of the ultrasound waves, the transmitting apertures of the ultrasound transducer groups, the focus positions corresponding to the ultrasound transducer groups and/or the time delays corresponding to the transducers in the ultrasound transducer groups may also be adjusted to obtain different transmitting parameters, so as to obtain ultrasound waves focused at different focus positions or steered in different angles. For example, in one embodiment, the transmitting apertures of the selected ultrasound transducer groups, the focus positions corresponding to the ultrasound transducer groups and/or the time delays corresponding to the transducers in the ultrasound transducer groups may be adjusted to obtain a first transmitting parameter and a second transmitting parameter respectively. The transmitting circuit may control the transducers in the ultrasound transducer groups according to the first transmitting parameter to transmit a first ultrasound wave, and control the transducers in the ultrasound transducer groups according to the second transmitting parameter to transmit a second ultrasound wave. The first transmitting parameter may be different from the second transmitting parameter. The transmitting parameter may include at least one of the transmitting aperture, the focus position corresponding to the ultrasound transducer group, and the relative time delay corresponding to the transducers in the ultrasound transducer group, etc.

Figure 6:
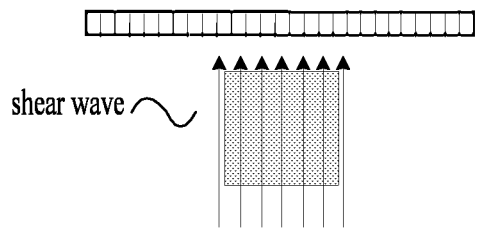
FIG. 6 is a schematic diagram of the receiving in FIG. 1.

In step S14, during the duration, the receiving circuit may control the ultrasound probe to receive the ultrasound echoes from the lateral positions in the region of interest to obtain the echo information at different positions in the region of interest at different times. The image processing may be performed on the echo information. For example, FIG. 6 shows a schematic diagram of the receiving, in which the shear wave propagates laterally through the region of interest, and the receiving beam covers multiple lateral positions within the region of interest.

Regarding the imaging processing, there may be multiple embodiments in step S14. For example, the imaging processing may be shear wave imaging processing, B-mode imaging processing or C-mode imaging processing, etc. It can be understood that, in actual implementation, for the image processing of different imaging modes, the transmitting sequence for transmitting the ultrasound waves and the receiving sequence for receiving the ultrasound echoes may be controlled differently, and the transmitting and receiving processes coordinate with each other. The transmitting sequence here may include the sequence of transmitting, time interval, number of transmitting, etc. In short, in one imaging process, the ultrasound waves may be transmitted for multiple times, or multiple types of ultrasound waves may be transmitted, and thereafter, the imaging processing may be performed on the echo information of each transmitting. The detailed description will be provided below in connection with different examples.

In addition, during the duration, the ultrasound echoes from the region of interest may be received to obtain echo information at different positions in the region of interest at different times, and the shear wave information corresponding to the region of interest may be obtained according to the echo information. This process may include:

during the duration, receiving the echoes of the first ultrasound wave and the echoes of the second ultrasound wave from the region of interest through the receiving circuit; and weighting the echo signals of the first ultrasound wave and the echo signals of the second ultrasound wave and obtaining the shear wave information corresponding to the region of interest according to the results of the weighting process. For example, the echo signals of the first ultrasound wave and the echo signals of the second ultrasound wave may be superimposed according to the weights.

Figure 7:
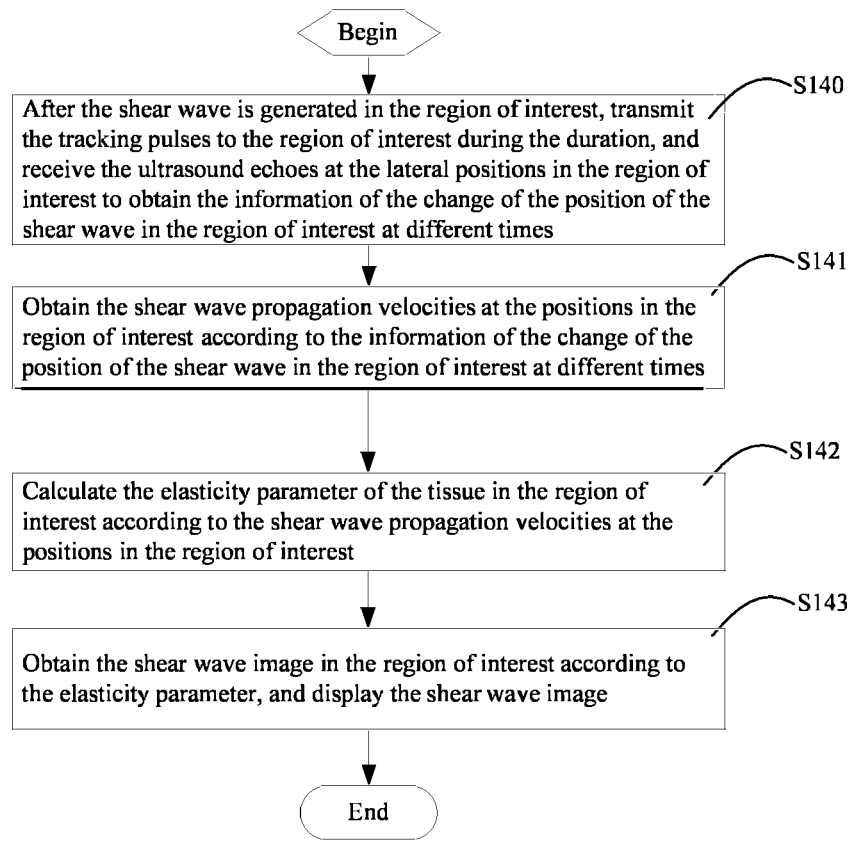
FIG. 7 is a schematic flowchart of one embodiment of the step S14 in FIG. 1.

FIG. 7 shows a schematic flowchart of one embodiment of step S14. In this embodiment, a shear wave imaging process is shown, in which the steps S11 to S14 may specifically include the following steps.

In step S140, after the shear wave is generated in the region of interest, the tracking pulses may be transmitted to the region of interest during the duration, and the ultrasound echoes at the lateral positions in the region of interest may be received to obtain the information of the change of the position of the shear wave in the region of interest at different times. For example, in an example, in order to accurately capture the propagation position of the shear wave, a high-density (that is, the width spacing between the beams may be small) receiving method may be used. For example, the beam spacing may be set to 0.2 mm. Alternatively, in order to reduce the amount of calculation, the spacing between beams may also be appropriately increased according to actual needs, such as 0.4 mm, 0.6 mm, 1 mm, and so on. When the shear wave propagates in the region of interest, the position of the shear wave in the region of interest may be obtained through one transmitting and receiving process.

In step S141, the shear wave propagation velocities at the positions in the region of interest may be obtained according to the information of the position of the shear wave in the region of interest at different times.

In step S142, the elasticity parameter of the tissue in the region of interest may be obtained according to the shear wave propagation velocities at the positions in the region of interest. The elasticity parameter may be the Young's modulus or the shear modulus.

In step S143, the shear wave image in the region of interest may be obtained according to the elasticity parameter, and may be displayed. In the present disclosure, the shear wave information may include one of the shear wave propagation velocity and elasticity parameter, etc.

Specifically, in one example, in step S10, the focused push pulses may be transmitted to the region of interest of the target tissue to generate the shear wave. The duration of the push pulse transmitting may be longer than that of the conventional ultrasound pulse transmitting, and may be about tens to hundreds of microseconds. The push pulses may generate a shear wave source at the focus position. The shear wave may be generated at the shear wave source and propagates in a direction different from the transmitting direction of the push pulses. In steps S11, S12 and S14, a series of tracking pulses may be transmitted to the region of interest and the echo information may be obtained. After the push pulses are transmitted to the target region and the shear wave is generated, a series of tracking pulses may be transmitted and the each information of each transmitting may be received to obtain the echo data of the tracking pulses in a propagation range in the region of interest within a period of time. The echo data may record the tissue information at the positions in the propagation range during the propagation of the shear wave.

It can be understood that the parameters for transmitting the tracking pulses at different times may be different. For example, the transmitting frequency, the transmitting waveform, the focus position, the focusing intensity or the transmitting aperture may be adjusted according to the actual situation. Generally, the receiving process may follow the transmitting process, and then another transmitting and receiving process may be started. In addition, the time interval between each transmitting/receiving group may also be set as needed.

After a period of detection, according to the echo information, the change of the position of the shear wave in the region of interest at various times, or the time difference between the times when the shear wave passes through any two lateral positions in the region of interest, may be obtained, so as to calculate the shear wave propagation velocities at various positions in the region of interest.

There is a specific relationship between the propagation velocity Cs of shear waves in an isotropic elastic tissue and the elastic modulus of the tissue: Young's modulus $E=3\Sigma Cs^2$, and shear modulus $G=\rho Cs^2$, where $\rho$ is the tissue density, Cs is the shear wave propagation velocity in the tissue. Therefore, the elasticity parameter (such as the Young's modulus) of the tissue may be calculated according to the shear wave propagation velocities at various positions in the region of interest, so as to obtain the shear wave images. Obtaining the shear wave image according to the calculated elasticity parameter may be known in the art, which will not be detailed here.

The obtained shear wave image of the region of interest may be displayed on the display.

It can be understood that, in this embodiment, the method may be used to perform elasticity measurement on the target tissue, where the shear wave imaging processing is one of the elasticity measurement methods. It can be understood that, in this embodiment, the elasticity measurement methods may be a vibration elasticity measurement method based on external force vibration, a shear wave measurement method based on acoustic radiation force or a strain elasticity measurement method, etc. Therefore, the shear wave in step S10 may be generated according to the elasticity measurement methods above.

Specifically, the vibration elasticity measurement method based on external force vibration may generate the shear waves propagating into the tissue through external force vibration, and detect the propagation parameter (such as the propagation velocity) of the shear wave in the tissue to represent the hardness difference between tissues. For an isotropic elastic tissue, there is a relationship between the propagation velocity Cs of the shear wave and the elastic modulus E of the tissue: Young's modulus $E=3\rho Cs^2$ (where, $\rho$ is the tissue density). In other words, there is a one-to-one correspondence between the shear wave velocity and the elastic modulus.

The shear wave measurement method based on the acoustic radiation force may generate the shear wave propagating in the tissue through the ultrasound acoustic radiation force, and then detect the propagation parameter (such as the propagation velocity) of the shear wave in the tissue to represent the difference in hardness between tissues. For an isotropic elastic tissue, there is a relationship between the propagation velocity Cs of the shear waves and the elastic modulus E of the tissue: Young's modulus $E=3\rho Cs^2$ (where, $\rho$ is the density of the tissue). In other words, there is a one-to-one correspondence between the shear wave velocity and the elastic modulus.

In the strain elasticity measurement method (or be referred to as conventional ultrasound elasticity measurement method), the target tissue may be slightly pressed by the probe or by means of the breathing or vascular pulsation processes or other processes of human body, and two frames of ultrasound echo signals before and after the compression. When the tissue is compressed, a strain along the compression direction will be generated in the tissue. If the Young's modulus distribution is not uniform in the tissue, the strain distribution in the tissue will also be different. The strain information of the tissue may be detected by certain methods, and the parameters related to the elasticity of the tissue such as the strain, the strain rate or the like may be calculated, so as to indirectly represent the elasticity difference between different tissues in the pressed area. Specifically, according to Hooke's law, for an isotropic elastomer, stress $\sigma$=strain $\varepsilon \times$Young's modulus E, i.e. $E=\sigma/\varepsilon$. Young's modulus is a parameter related to the hardness of the tissue. The higher the Young's modulus, the greater the hardness of the tissue.

It should be noted that, in the present embodiment, the method for generating the shear waves will not be limited to those described above. Other methods may also be used. In other words, the method for tracking and detecting the shear waves proposed in the present disclosure may not be limited to be applied in the elasticity measurement methods above, but may also be applied to other elasticity measurement methods based on ultrasound elastography.

Figure 8:
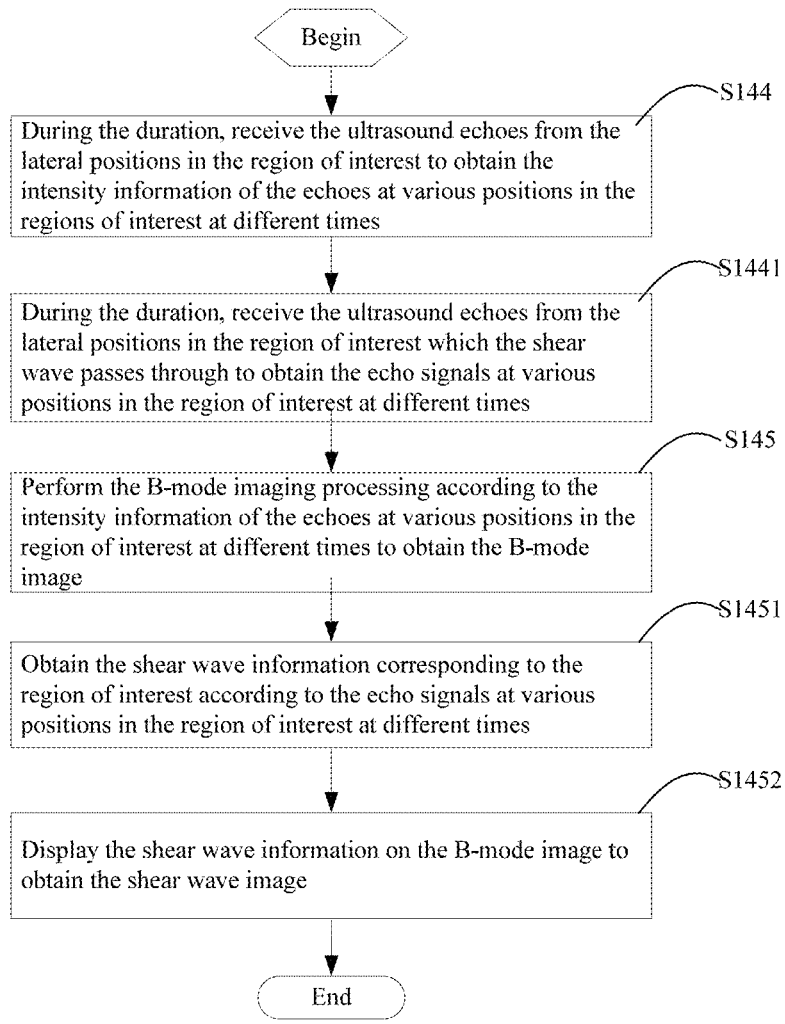
FIG. 8 is a schematic flowchart of another embodiment of the step S14 in FIG. 1.

FIG. 8 is a schematic flowchart of another embodiment of step S14. In this embodiment, the process for tracking and detecting the shear wave may further include a B-mode imaging process. The transmitting and receiving processes of the B-mode imaging may be interspersed in the processes from the step S10 to step S14. For example, the transmitting and receiving for obtaining at least one frame or multiple frames of B-mode image data may be performed, followed by the detection process for at least one frame of shear wave image (including the steps S11, S12 and S14).

The process of performing the step S14 may further include the following steps.

In step S144, during the duration, the ultrasound echoes from the lateral positions in the region of interest may be received to obtain the intensity information of the echoes at various positions in the regions of interest at different times.

In step S1441, during the duration, the ultrasound echoes from the lateral positions in the region of interest which the shear wave passes through may be received to obtain the echo signals at various positions in the region of interest at different times.

In step S145, the B-mode imaging processing may be performed according to the intensity information of the echoes at various positions in the region of interest at different times to obtain a B-mode image.

In step S1451, the shear wave information corresponding to the region of interest may be obtained according to the echo signals at various positions in the region of interest at different times.

In step S1452, the shear wave information may be displayed on the B-mode image to obtain the shear wave image.

Specifically, in an example, in order to perform B-mode imaging processing, the ultrasound transducer group may be selected to transmit the ultrasound waves for multiple times to obtain corresponding echoes. Specifically, the focus position (lateral position) of different transmitting may be different, thereby obtaining the echo information at different lateral positions. The B-mode imaging processing may be performed according to the echo information.

Figure 9:
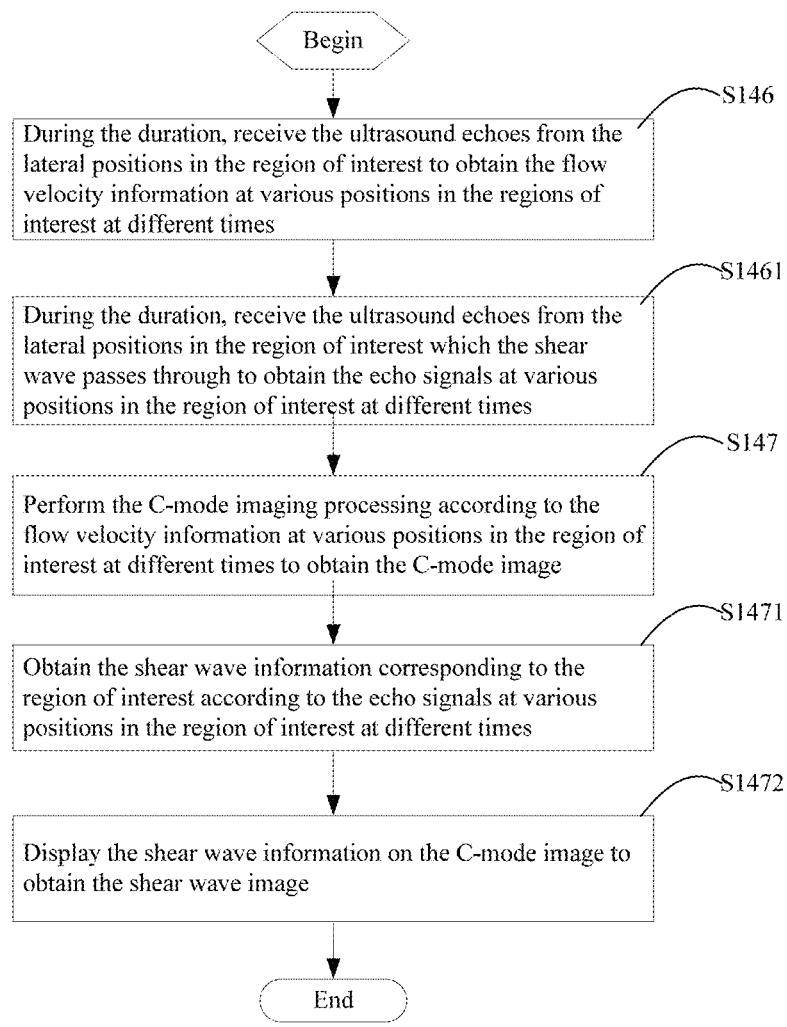
FIG. 9 is a schematic flowchart of another embodiment of the step S14 in FIG. 1.

FIG. 9 is a schematic flow chart of another embodiment of step S14. In this embodiment, the process for tracking and detecting the shear wave may further include a C-mode imaging process. The transmitting and receiving processes of the C-mode imaging may be interspersed in the processes from the step S10 to step S14. For example, the transmitting and receiving for obtaining at least one frame or multiple frames of C-mode image data may be performed, followed by the detection process for at least one frame of shear wave image (including the steps S11, S12 and S14). The process of performing the step S14 may further include the following steps.

In step S146, during the duration, the ultrasound echoes from the lateral positions in the region of interest may be received to obtain the flow velocity information at positions in the regions of interest at different times.

In step S1461, during the duration, the ultrasound echoes from the lateral positions in the region of interest which the shear wave passes through may be received to obtain the echo signals at various positions in the region of interest at different times.

In step S147, the C-mode imaging processing may be performed according to the flow velocity information at positions in the regions of interest at different times to obtain a C-mode image.

In step S1471, the shear wave information corresponding to the region of interest may be obtained according to the echo signals at various positions in the region of interest at different times.

In step S1472, the shear wave information may be displayed on the C-mode image to obtain the shear wave image.

Therefore, the methods for imaging in ultrasound scanning provided by the present disclosure may be not only applicable to shear wave imaging modes, but also applicable to other imaging modes, such as B-mode imaging, C-mode imaging, and the like.

For example, in one embodiment, the receiving for the shear wave detection or the receiving of the echo signals in the B-mode imaging or the C-mode imaging may be performed using the following methods. For example, in the process of receiving the ultrasound echoes from the region of interest in the steps above, the ultrasound echoes from the lateral range of the region of interest may be received, where the lateral range may be greater than or equal to the width of the region of interest in the shear wave propagation direction. The lateral range may be the range in the shear wave propagation direction.

When receiving the ultrasound echoes from the region of interest, multiple transducers in the ultrasound probe may be used to receive the ultrasound echoes from the region of interest.

Further, in step S14, receiving the ultrasound echoes from the region of interest to obtain the echo information at different positions in the region of interest at different times during the duration may include:

changing (e.g., increasing) the receiving density of the ultrasound echoes in the lateral range in the region of interest; and during the duration, receiving the ultrasound echoes from the region of interest according to the receiving density to obtain the echo information at different positions in the region of interest at different times.

For example, in one embodiment, the beam spacing corresponding to the receiving density may be selected a range of 0-1 mm. The receiving density herein may be understood as the distribution of the ultrasound receiving beams in the lateral range of the region of interest.

Figure 10:
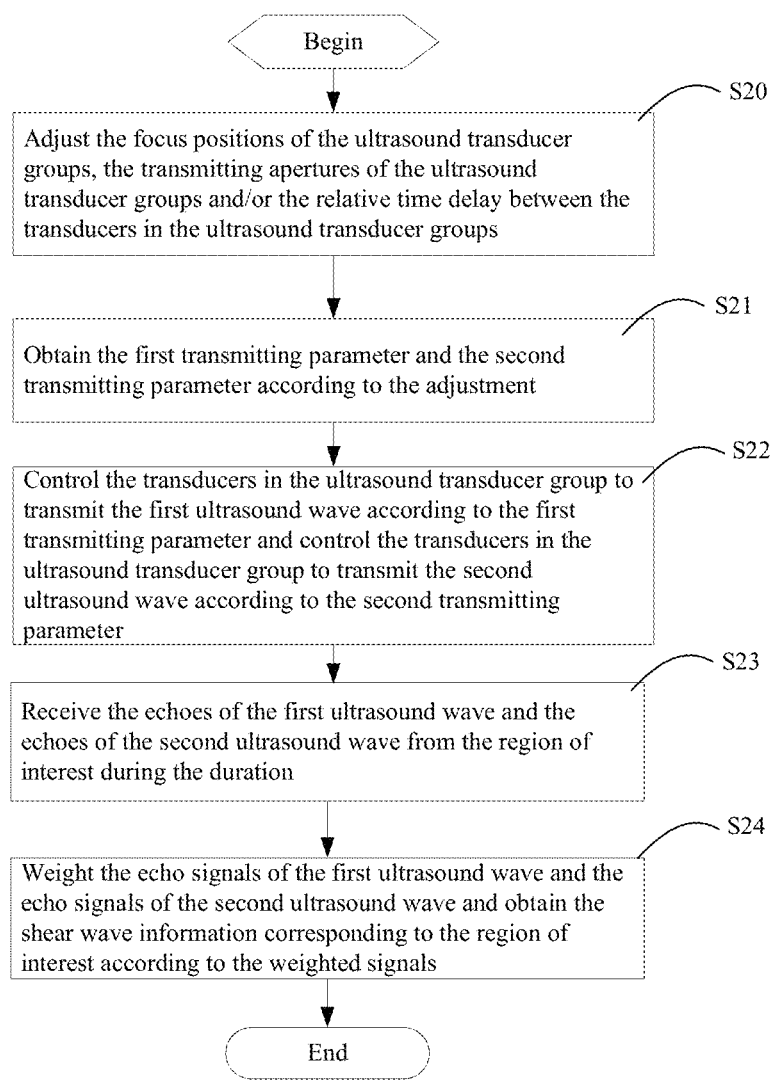
FIG. 10 is a schematic flowchart of another embodiment of the method for imaging in ultrasound scanning provided by the present disclosure.

FIG. 10 is a schematic flowchart of another embodiment of the method for imaging in ultrasound scanning provided by the present disclosure. In this embodiment, the method may further include the following steps.

In step S20, the number of the selected ultrasound transducer group, the focus positions of the ultrasound transducer groups, the transmitting aperture of the ultrasound transducer group and the relative time delay between the transducers in the ultrasound transducer group may be adjusted. For example, in some examples, the ultrasound waves may be transmitted with different steering angles, with different transmitting apertures or with different focus positions. In Step S21, a first transmitting parameter and a second transmitting parameter are obtained according to the adjustment.

In step S22, the ultrasound waves may be transmitted according to the adjusted parameters, and, during the duration, an ultra-wide beam receiving of the ultrasound echoes at the lateral positions in the region of interest may be performed to obtain the echo information at different positions in the region of interest at different times. In Step S23, the echoes of the first ultrasound wave and the echoes of the second ultrasound wave from the region of interest are received during the duration.

In step S24, the echo information before and after the adjustment may be weighted and imaging processing may be performed on the weighted echo information.

Figure 11:
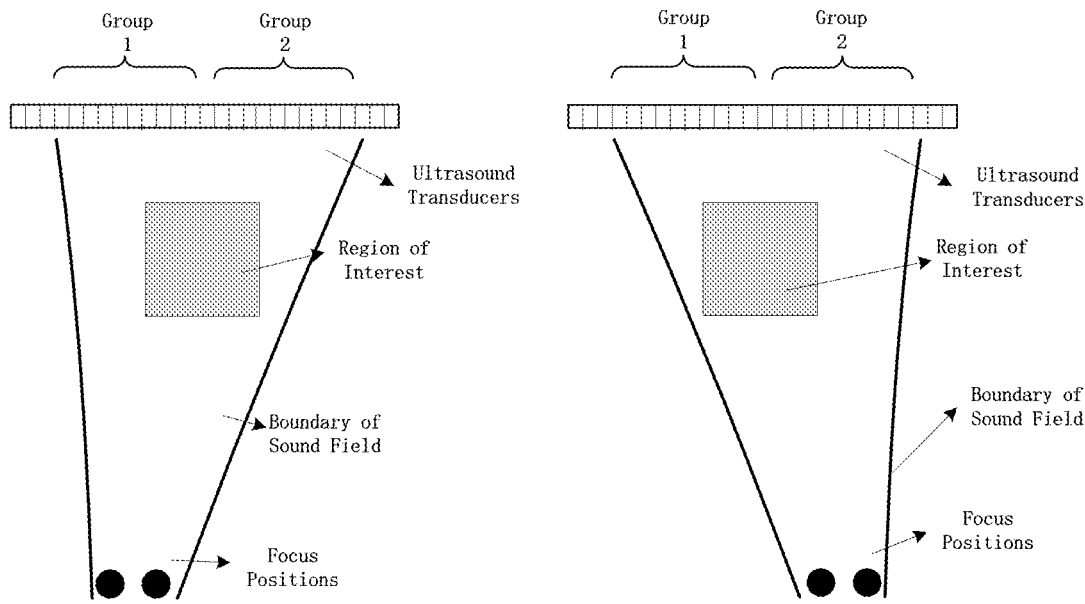
FIG. 11 is a schematic diagram of adjusting the ultrasound parameters and performing the weighting processing in FIG. 10.

FIG. 11 is a schematic diagram of adjusting the ultrasound parameters and weighting the echo information in FIG. 10. It can be seen that the schematic diagram on the right is different from the schematic diagram on the left at least in the focus position and the steering angle. Weighting the echo information obtained by the two ultrasound transmitting can improve the SNR of the echo signal, thereby improving the quality of the echo signal.

In the methods of the present disclosure, such as in the process of implementing the shear wave imaging, after the shear wave is generated, the system may continuously transmit a series of detection ultrasound waves to the region of interest in a certain period of time and receive the corresponding echo signal, and obtain and display the elasticity parameter the region of interest through the shear wave elastic imaging calculation. In the transmitting and receiving of the ultrasound waves, the system may select special transmitting focus control parameters according to the size and position of the region of interest to transmit the ultrasound waves to the target tissue to form an ultra-wide sound field in the region of interest, and receive the corresponding ultrasound echo signals to obtain the information of the region of interest in the ultra-wide range. With the methods of the present disclosure, the information of the region of interest in a large range may be obtained with smaller number of transmitting, which greatly improves the frame rate. Therefore, the information of the target tissue at various times may be obtained with a higher time resolution in the detection time. Accordingly, the propagation positions of the shear wave at various times and thereby the propagation velocities at the positions may be accurately calculated.

Figure 12:
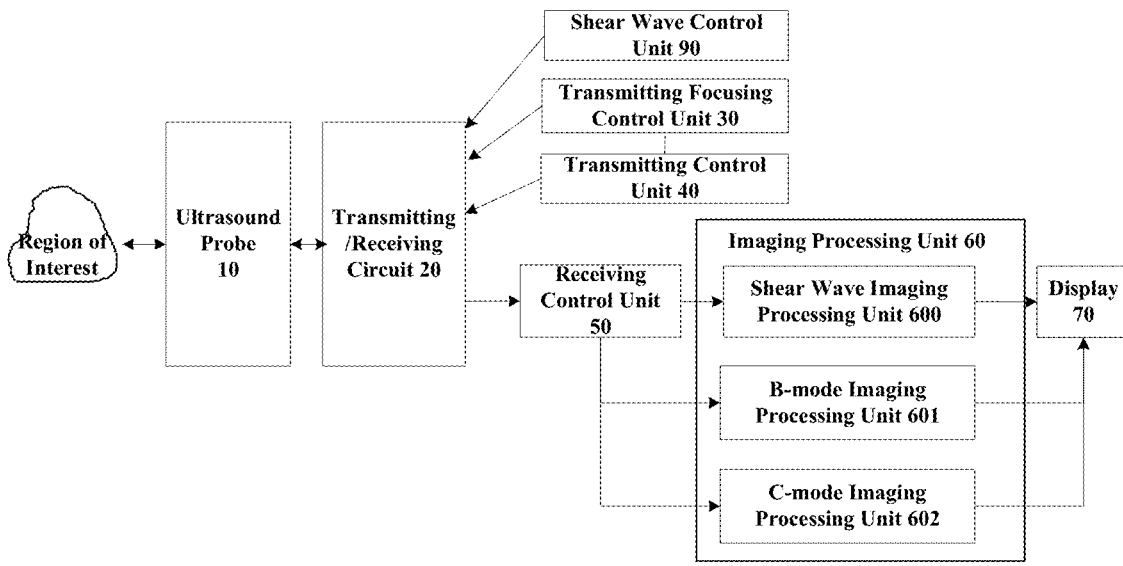
FIG. 12 is a schematic block diagram of one embodiment of a system for imaging in ultrasound scanning provided by the present disclosure.

FIG. 12 shows a schematic block diagram of one embodiment of the ultrasound imaging system provided by the present disclosure. In this embodiment, the system may include an ultrasound probe 10, a transmitting and receiving circuit 20, a shear wave control unit 90, a transmitting focusing control unit 30, a transmitting control unit 40, a receiving control unit 50, an imaging processing unit 60 and a display 70.

The ultrasound probe 10 may include at least one ultrasound transducer group.

The transmitting and receiving circuit 20 may be configured to excite the probe to transmit the ultrasound beam to the target tissue and receive the echoes of the ultrasound beam to obtain the echo signals. The transmitting circuit may send the delay-focused ultrasound pulses with a certain amplitude and polarity to the probe. The probe may be excited by the ultrasound pulses to transmit the ultrasound waves to the target tissue (not shown in the figure, such as heart tissue, etc.) being examined. After a certain delay, the probe may receive the ultrasound echoes carrying the information of the tissue reflected from the target area and convert the ultrasound echoes into electrical signals. The receiving circuit may receive the electrical signals converted by the probe to obtain the ultrasound echo signals.

The shear wave control unit 90 may be configured to control the ultrasound probe through the transmitting and receiving circuit 20 to generate the shear wave in the target tissue which propagates to the region of interest.

The transmitting focusing control unit 30 may be configured to select at least one ultrasound transducer group in the ultrasound probe and determine the focus points and transmitting aperture of the ultrasound transducer group according to the depth and width of the region of interest in the target tissue, such that the sound field generated by the at least one ultrasound transducer group completely covers the region of interest in the target tissue.

The transmitting control unit 40 may be configured to determine the relative time delay between the transmitting of the transducers in the ultrasound transducer groups and control the transducers in the ultrasound transducer group through the transmitting and receiving circuit 20 to transmit the ultrasound waves according to the time delay, such that the ultrasound waves transmitted by the transducers in the ultrasound transducer group can arrive their corresponding focus positions at the same time, thereby achieving the transmitting focusing.

The receiving control unit 50 may be configured to receive the ultrasound echoes from the region of interest through the transmitting and receiving circuit 20 during the duration to obtain the echo information at different positions in the region of interest at different times.

The imaging processing unit 60 may be configured to obtain the shear wave information corresponding to the region of interest according to the echo information obtained by the receiving control unit 50 to perform imaging processing.

The display 70 may be configured to display the image generated by the imaging processing unit 60.

The shear wave control unit 90, the transmitting focusing control unit 30, the transmitting control unit 40, the receiving control unit 50 and the imaging processing unit 60 may be implemented with one or more processors.

The processes in the steps S10 to S14 above may be implemented by a computer program. The computer program may be stored in the memory. One or more processors may execute the computer program stored in the memory to perform the processes in the steps S10 to S14, thereby implementing the shear wave control unit 90, the transmitting focusing control unit 30, the transmitting control unit 40, the receiving control unit 50 and the imaging processing unit 60. Regarding the detailed description of the processes from step S10 to step S14 in the following, reference may be made to the description above. The processor herein may include the processor itself and the peripheral circuits thereof.

Figure 13:
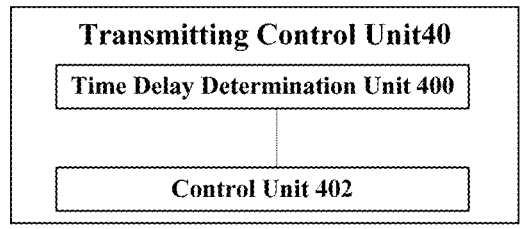
FIG. 13 is a schematic block diagram of the transmitting control unit in FIG. 12.

Referring to FIG. 13, the transmitting control unit 40 may include:

a time delay determination unit 400 which may be configured to calculate the time difference between the times when the ultrasound waves transmitted by the transducers arrive the focus position according to the geometric relationship between the focus position and the ultrasound probe, and compensate the start time of the transmitting, thereby determining the relative time delay between the transmitting of the transducers in the ultrasound transducer group; and a control unit 402 which may be configured to control the transducers to transmit the ultrasound waves for tracking to the region of interest according to the relative time delay.

In one embodiment, the receiving control unit 50 may further be configured to receive the ultrasound echoes from the lateral range of the region of interest. The lateral range may be greater than or equal to the width of the region of interest in the shear wave propagation direction.

In one embodiment, there may be multiple ultrasound transducer groups respectively corresponding to multiple focus positions. The multiple focus positions may be arranged laterally along the shear wave propagation direction.

In one embodiment, at least one sound field corresponding to the at least one ultrasound transducer group may be focused at the corresponding focus position, and the at least one sound field may be superimposed to form the sound field completely covering the region of interest.

In one embodiment, the depth of the focus positions corresponding to the ultrasound transducer group determined by the transmitting focusing control unit 30 may be greater than the depth of the region of interest.

Alternatively, the depth of the focus positions corresponding to the ultrasound transducer group determined by the transmitting focusing control unit 30 may be in the depth range of the region of interest, and the width formed by all focus positions arranged along the shear wave propagation direction may be larger than the width of the region of interest.

In one embodiment, the receiving control unit may include:

a receiving density adjustment unit (not shown) which may be configured to adjust the receiving density of ultrasound echoes in the lateral range in the region of interest. For example, the receiving density of the ultrasound echoes in the lateral range in the region of interest may be increased. During the duration, the ultrasound echoes from the region of interest may be received according to the receiving density to obtain the echo information at different positions in the region of interest at different times.

In one embodiment, the information obtained by the receiving control unit 30 may be the information of the change of the position of the shear wave in the region of interest at different times.

The imaging processing unit 60 may include a shear wave imaging processing unit 600 which may be configured to obtain the shear wave propagation velocities at positions in the region of interest according to the information of the change of the position of the shear wave in the region of interest at different times, so as to obtain the elasticity parameter of the tissue in the region of interest.

In another embodiment, the information obtained by the receiving control unit 30 may be the intensity information of echoes at various positions in the region of interest at different times.

The imaging processing unit 60 may include a B-mode imaging processing unit 601 which may be configured to perform the B-mode imaging processing according to the intensity information of the echoes at various positions in the region of interest at different times. It can be understood that the B-mode imaging processing unit 601 may coexist with the shear wave imaging processing unit 600, and the B-mode imaging process may be added to the tracking detection process of the shear wave. The transmitting and receiving processes of the B-mode imaging in the B-mode imaging processing unit 601 may be interspersed with the shear wave imaging process in the shear wave imaging processing unit 600.

In another embodiment, the information obtained by the receiving control unit 30 may be the flow velocity information at the positions in the region of interest at different times.

The imaging processing unit 60 may include a C-mode imaging processing unit 602 which may be configured to perform the C-mode imaging processing according to the flow velocity information at the positions in the region of interest at different times. It can be understood that the C-mode imaging processing unit 602 may coexist with the shear wave imaging processing unit 600, and the C-mode imaging process may be added to the tracking detection process of the shear wave. The transmitting and receiving processes of the C-mode imaging in the C-mode imaging processing unit 602 may be interspersed with the shear wave imaging process in the shear wave imaging processing unit 600.

Figure 14:
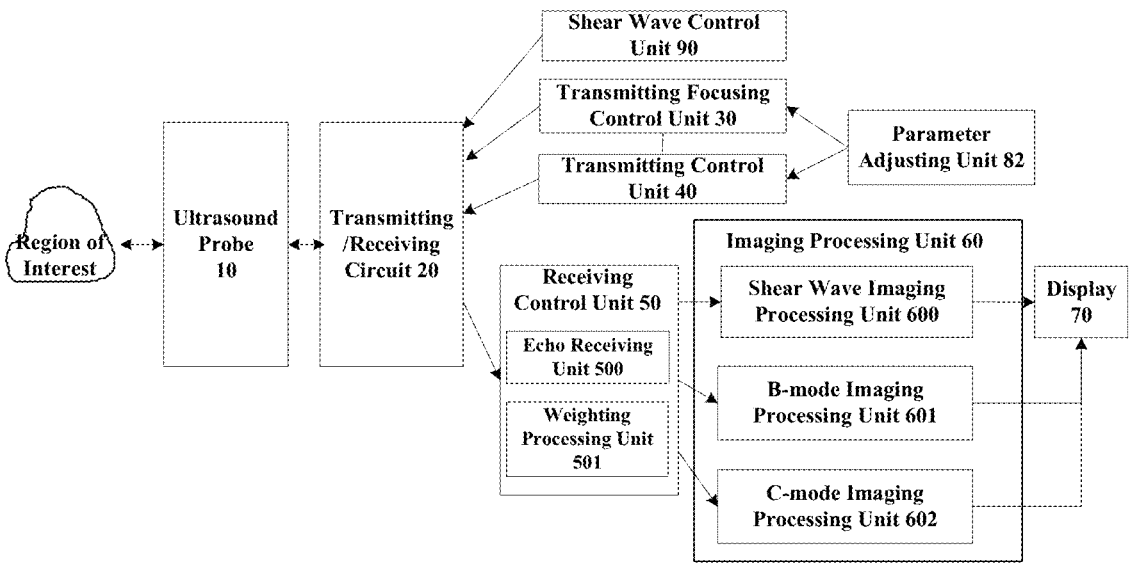
FIG. 14 is a schematic block diagram of another embodiment of the system for imaging in ultrasound scanning provided by the present disclosure.
Figure 15:
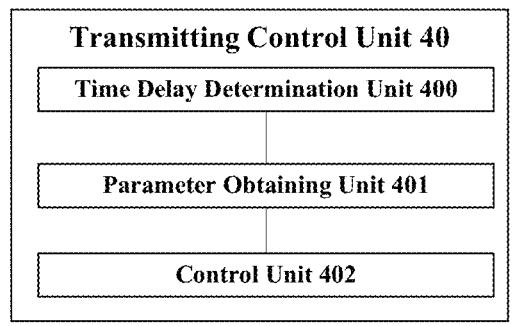
FIG. 15 is a schematic block diagram of the transmitting control unit in FIG. 14.

FIG. 14 shows a schematic block diagram of another embodiment of the ultrasound imaging system provided by the present disclosure. In connection with FIG. 15, in this embodiment, the system may further include:

an adjusting unit 82 which may be configured to adjust the transmitting aperture of the selected ultrasound transducer group, the focus position corresponding to the ultrasound transducer group, and/or the relative time delay corresponding to the transducers in the ultrasound transducer group.

The transmitting control unit 40 may further include a parameter obtaining unit 401 which may be configured to obtain the first transmitting parameter and the second transmitting parameter according to the adjustment of the adjustment unit 82.

The control unit 402 in the transmitting control unit 40 may be configured to control the transducers in the ultrasound transducer group to transmit the first ultrasound wave according to the first transmitting parameter and control the transducers in the ultrasound transducer group to transmit the second ultrasound wave according to the second transmitting parameter.

The receiving control unit 50 may include:

an echo receiving unit 500 which may be configured to receive the echoes of the first ultrasound wave and the echoes of the second ultrasound wave from the region of interest during the duration; and a weighting processing unit 501 which may be configured to weight the echo signals of the first ultrasound wave and the echo signals of the second ultrasound wave and obtain the shear wave information corresponding to the region of interest according to the weighted signals.

It can be understood that other functional units in FIG. 14 may have the same principle as the corresponding functional units in FIG. 12, and reference may be made to the description of FIG. 12 above.

An apparatus for imaging in ultrasound scanning may be provided in the present disclosure. The apparatus may include: a shear wave control unit which may be configured to generate the shear wave in the target tissue which propagates in the region of interest;

a transmitting focusing control unit which may be configured to select at least one ultrasound transducer group in the ultrasound probe and determine the focus points and transmitting aperture of the ultrasound transducer group according to the depth and width of the region of interest in the target tissue, such that the sound field generated by the at least one ultrasound transducer group completely covers the region of interest in the target tissue;

a transmitting control unit which may be configured to determine the relative time delay between the transmitting of the transducers in the ultrasound transducer groups and control the transducers in the ultrasound transducer group to transmit the ultrasound waves according to the time delay, such that the ultrasound waves transmitted by the transducers in the ultrasound transducer group can arrive their corresponding focus positions at the same time, thereby achieving the transmitting focusing;

a receiving control unit which may be configured to receive the ultrasound echoes from the region of interest during the duration to obtain the echo information at different positions in the region of interest at different times; and an imaging processing unit 60 which may be configured to obtain the shear wave information corresponding to the region of interest according to the echo information obtained by the receiving control unit.

In one embodiment, the transmitting control unit may include:

a time delay determination unit which may be configured to calculate the time difference between the times when the ultrasound waves transmitted by the transducers arrive the focus position according to the geometric relationship between the focus position and the ultrasound probe, and compensate the start time of the transmitting, thereby determining the relative time delay between the transmitting of the transducers in the ultrasound transducer group; and a control unit which may be configured to control the transducers to transmit the ultrasound waves for tracking to the region of interest according to the relative time delay.

In one embodiment, the receiving control unit may further be configured to receive the ultrasound echoes from the lateral range in the region of interest. The lateral range may be greater than or equal to the width of the region of interest in the shear wave propagation direction.

In one embodiment, there may be multiple ultrasound transducer groups respectively corresponding to multiple focus positions. The multiple focus positions may be arranged laterally along the shear wave propagation direction.

In one embodiment, at least one sound field corresponding to the at least one ultrasound transducer group may be focused at the corresponding focus position, and the at least one sound field may be superimposed to form the sound field completely covering the region of interest.

In one embodiment, the depth of the focus positions corresponding to the ultrasound transducer group determined by the transmitting focusing control unit may be greater than the depth of the region of interest.

Alternatively, the depth of the focus positions corresponding to the ultrasound transducer group determined by the transmitting focusing control unit may be in the depth range of the region of interest, and the width formed by all focus positions arranged along the shear wave propagation direction may be larger than the width of the region of interest.

In one embodiment, the receiving control unit may include:

a receiving density adjustment unit which may be configured to adjust the receiving density of ultrasound echoes in the lateral range in the region of interest.

In one embodiment, the apparatus may further include:

an adjusting unit which may be configured to adjust the transmitting aperture of the selected ultrasound transducer group, the focus position corresponding to the ultrasound transducer group, and/or the relative time delay corresponding to the transducers in the ultrasound transducer group.

The transmitting control unit may further include a parameter obtaining unit which may be configured to obtain the first transmitting parameter and the second transmitting parameter according to the adjustment of the adjustment unit.

The control unit in the transmitting control unit may be configured to control the transducers in the ultrasound transducer group to transmit the first ultrasound wave according to the first transmitting parameter and control the transducers in the ultrasound transducer group to transmit the second ultrasound wave according to the second transmitting parameter.

In one embodiment, the receiving control unit may include:

an echo receiving unit which may be configured to receive the echoes of the first ultrasound wave and the echoes of the second ultrasound wave from the region of interest during the duration; and a weighting processing unit which may be configured to weight the echo signals of the first ultrasound wave and the echo signals of the second ultrasound wave and obtain the shear wave information corresponding to the region of interest according to the weighted signals.

For more details, reference may be made to the description of FIG. 1 to FIG. 15 above.

In the methods, apparatuses and systems for imaging in ultrasound scanning provided in the present disclosure, at least one ultrasound transducer group in the ultrasound probe may be selected and the focus position and transmitting aperture of the ultrasound transducer group may be determined according to the depth and width of the region of interest such that the sound field generated by the at least one ultrasound transducer group completely covers the region of interest in the target tissue. The transducers in the ultrasound transducer group may be controlled to transmit the ultrasound waves according to the corresponding relative time delay such that the ultrasound waves transmitted by the transducers in the ultrasound transducer group arrive the corresponding focus point at the same time to achieve the transmitting focusing. Therefore, the ultrasound energy in the region of interest is uniform, and accurate echo information can be obtained.

Furthermore, by adjusting the parameters of ultrasound scanning and weighting the echo signals obtained under different parameters, the signal-to-noise ratio of the echo signals can be improved, thereby improving the signal quality.

Moreover, the methods, apparatuses and systems in the embodiments of the present disclosure can be widely applied in many applications, such as shear wave imaging, B-mode imaging and C-mode imaging, etc. The applications are very extensive.

A person ordinarily skilled in the art will understand that all or part of the processes in the methods in the embodiments above may be implemented by instructing the hardware through a computer program. The program may be stored in a computer-readable storage medium. When the program is executed, the processes of the methods in the embodiments above may be performed. The storage medium may be a magnetic disk, an optical disk, a read-only memory (ROM) or a random access memory (RAM), etc.

The present disclosure has been described in detail in connection with specific embodiments. However, it cannot be assumed that the present disclosure will be limited to the descriptions. For a person ordinarily skilled in the art, without departing from the concept of the present disclosure, many simple deductions or replacements may be made, which should all fall in the protection scope of the present disclosure.

The invention claimed is:

1. An ultrasound imaging method, comprising:
generating a shear wave in a target tissue which propagates in a region of interest in a shear wave propagation direction;
selecting a plurality of ultrasound transducer groups from multiple ultrasound transducer groups in an ultrasound probe;
determining a number of the plurality of ultrasound transducer groups, a number of focus points, and a focus position and a transmitting aperture of each of the plurality of ultrasound transducer groups, according to a depth and a width of the region of interest in the target tissue, wherein
a depth of the focus position corresponding to each of the plurality of ultrasound transducer groups is greater than the depth of the region of interest, and a width formed by all focus points corresponding to the plurality of ultrasound transducer groups and arranged along the shear wave propagation direction is greater than the width of the region of interest, or
a depth of the focus position corresponding to each of the plurality of ultrasound transducer groups is within a depth range of the region of interest, and a width formed by all focus points corresponding to the plurality of ultrasound transducer groups and arranged along the shear wave propagation direction is greater than the width of the region of interest;
controlling, according to the determined number of the plurality of ultrasound transducer groups, the determined number of focus points, the determined focus position and transmitting aperture of each of the plurality of ultrasound transducer groups, transducers in the plurality of ultrasound transducer groups to transmit, to the target tissue, ultrasound waves that arrive at the corresponding focus points simultaneously, to form a sound field that completely covers the region of interest in the target tissue;
receiving ultrasound echoes of the ultrasound waves from the region of interest to obtain echo information in the region of interest; and
obtaining a shear wave information corresponding to the region of interest according to the echo information.

2. The ultrasound imaging method of claim 1, wherein the receiving the ultrasound echoes of the ultrasound waves from the region of interest comprises: receiving the ultrasound echoes from a lateral range in the region of interest, wherein the lateral range is greater than or equal to the width of the region of interest in the shear wave propagation direction.

3. The ultrasound imaging method of claim 1, wherein, the plurality of ultrasound transducer groups generate multiple sound fields, and the multiple sound fields superimpose to each other to form the sound field that completely covers the region of interest.

4. The ultrasound imaging method of claim 1, wherein the controlling the transducers in the plurality of ultrasound transducer groups to transmit the ultrasound waves to the target tissue comprises:
performing an adjustment on the transmitting aperture of each of the plurality of ultrasound transducer groups, the focus position corresponding to each of the plurality of ultrasound transducer groups, and a relative time delay corresponding to each of the transducers in the plurality of ultrasound transducer groups;
obtaining a first transmitting parameter and a second transmitting parameter according to the adjustment; and
controlling the transducers in the plurality of ultrasound transducer groups to transmit a first ultrasound wave according to the first transmitting parameter, and controlling the transducers in the plurality of ultrasound transducer groups to transmit a second ultrasound wave according to the second transmitting parameter, wherein the first ultrasound wave and the second ultrasound wave arrive at focus positions respectively at a same time; and wherein the receiving the ultrasound echoes of the ultrasound waves from the region of interest to obtain the echo information in the region of interest and the obtaining the shear wave information corresponding to the region of interest according to the echo information comprises:
receiving echo signals of the first ultrasound wave and echo signals of the second ultrasound wave from the region of interest; and
weighting the echo signals of the first ultrasound wave and the echo signals of the second ultrasound wave, and obtaining the shear wave information corresponding to the region of interest according to the weighted echo signals of the first ultrasound wave and the weighted echo signals of the second ultrasound wave.

5. The ultrasound imaging method of claim 1, wherein the receiving the ultrasound echoes of the ultrasound waves from the region of interest to obtain the echo information in the region of interest comprises:
increasing a receiving density of the ultrasound echoes in a lateral range in the region of interest; and
receiving the ultrasound echoes from the region of interest according to the increased receiving density to obtain the echo information in the region of interest.

6. The ultrasound imaging method of claim 5, wherein a beam spacing corresponding to the increased receiving density is selected in a range of 0-1 mm.

7. The ultrasound imaging method of claim 1, wherein:
each of the plurality of ultrasound transducer groups comprises a plurality of transducers; and
an ultrasound transducer group in the plurality of ultrasound transducer groups, that is further away from the focus points compared to a distance from the focus points of others of the plurality of ultrasound transducer groups, comprises more transducers.

8. The ultrasound imaging method of claim 1, wherein the focus points correspond to the plurality of ultrasound transducer groups and are on a straight line or curve.

9. An ultrasound imaging system, comprising:
an ultrasound probe which comprises multiple ultrasound transducer groups;
a transmitting and receiving circuit which excites the ultrasound probe to transmit an ultrasound beam to a target tissue and receive echoes of the ultrasound beam to obtain echo signals;
a memory which stores a computer program;
a processor which executes the computer program in the memory to:
control the ultrasound probe through the transmitting and receiving circuit to generate a shear wave in the target tissue which propagates in a region of interest in a shear wave propagation direction;
select a plurality of ultrasound transducer groups from the multiple ultrasound transducer groups;
determine a number of the plurality of ultrasound transducer groups, a number of focus points, and a focus position and a transmitting aperture of each of the plurality of ultrasound transducer groups, according to a depth and a width of the region of interest in the target tissue, wherein
a depth of the focus position corresponding to each of the plurality of ultrasound transducer groups is greater than the depth of the region of interest, and a width formed by all focus points corresponding to the plurality of ultrasound transducer groups and arranged along the shear wave propagation direction is greater than the width of the region of interest, or
a depth of the focus position corresponding to each of the plurality of ultrasound transducer groups is within a depth range of the region of interest, and a width formed by all focus points corresponding to the plurality of ultrasound transducer groups and arranged along the shear wave propagation direction is greater than the width of the region of interest;
control, according to the determined number of the plurality of ultrasound transducer groups, the determined number of focus points, the determined focus position and transmitting aperture of each of the plurality of ultrasound transducer groups, transducers in the plurality of ultrasound transducer groups to transmit, to the target tissue, ultrasound waves that arrive at the corresponding focus points simultaneously, to form a sound field that completely covers the region of interest in the target tissue;
receive ultrasound echoes of the ultrasound waves from the region of interest to obtain echo information in the region of interest; and
obtain a shear wave information corresponding to the region of interest according to the echo information; and
a display which displays an image generated by the processor.

10. The ultrasound imaging system of claim 9, wherein the processor is configured to receive the ultrasound echoes from a lateral range in the region of interest, wherein the lateral range is greater than or equal to the width of the region of interest in the shear wave propagation direction.

11. The ultrasound imaging system of claim 9, wherein the plurality of ultrasound transducer and to multiple focus positions, and the multiple focus positions are arranged laterally along the shear wave propagation direction.

12. The ultrasound imaging system of claim 11, wherein, the plurality of ultrasound transducer groups are configured to generate multiple sound fields, and the multiple sound fields superimpose to each other to form the sound field completely covering the region of interest.

13. The ultrasound imaging system of claim 9, wherein the processor further adjusts a receiving density of the ultrasound echoes in a lateral range in the region of interest.

14. The ultrasound imaging system of claim 9, wherein the processor controls the transducers in the plurality of ultrasound transducer groups through the transmitting and receiving circuit to transmit the ultrasound waves to the target tissue by:
performing an adjustment on the transmitting aperture of each of the plurality of ultrasound transducer groups, the focus position corresponding to each of the plurality of ultrasound transducer groups, and a relative time delay corresponding to each of the transducers in the plurality of ultrasound transducer groups;
obtaining a first transmitting parameter and a second transmitting parameter according to the adjustment; and
controlling the transducers in the plurality of ultrasound transducer groups through the transmitting and receiving circuit to transmit a first ultrasound wave according to the first transmitting parameter, and controlling the transducers in the plurality of ultrasound transducer groups through the transmitting and receiving circuit to transmit a second ultrasound wave according to the second transmitting parameter, wherein the first ultrasound wave and the second ultrasound wave arrive at focus positions respectively at a same time.

15. The ultrasound imaging system of claim 14, wherein the processor receives the ultrasound echoes of the ultrasound waves from the region of interest through the transmitting and receiving circuit to obtain the echo information in the region of interest and obtains the shear wave information corresponding to the region of interest according to the echo information by:

receiving first echo signals of the first ultrasound wave and second echo signals of the second ultrasound wave from the region of interest through the transmitting and receiving circuit; and weighting the first echo signals of the first ultrasound wave and the second echo signals of the second ultrasound wave, and obtaining the shear wave information corresponding to the region of interest according to the weighted first echo signals of the first ultrasound wave and the weighted second echo signals of the second ultrasound wave.

16. The ultrasound imaging system of claim 9, wherein: the focus points are on a curve.

* * * * *